United States Patent

Dürr et al.

[11] Patent Number: 5,549,677
[45] Date of Patent: Aug. 27, 1996

[54] IMPLANT WITH PRESSING SURFACE

[75] Inventors: Walter Dürr, Panoramastrasse 5, D7537 Remchingen; Axel Kirsch, Talstrasse 23, D7024 Filderstradt, both of Germany

[73] Assignees: Walter Durr, Remchingen; Axel Kirsch, Filderstradt, both of Germany

[21] Appl. No.: 299,639

[22] Filed: Sep. 2, 1994

Related U.S. Application Data

[63] Continuation of Ser. No. 969,857, filed as PCT/DE92/00291 Apr. 7, 1992 published as WO92/20298 Nov. 26, 1992, abandoned.

[30] Foreign Application Priority Data

May 13, 1991 [DE] Germany ................ 41 15 959.4

[51] Int. Cl.⁶ ................. A61F 2/28; A61B 17/86
[52] U.S. Cl. ................. 623/16; 606/73; 606/105; 433/174; 411/397
[58] Field of Search ................ 623/16, 18; 433/174, 433/173; 411/433, 384, 397; 606/73, 105

[56] References Cited

U.S. PATENT DOCUMENTS

| | | | |
|---|---|---|---|
| 2,494,229 | 1/1950 | Collison | 606/73 |
| 4,259,072 | 3/1981 | Hirabayashi et al. | 623/16 X |
| 4,552,532 | 11/1985 | Mozsary . | |
| 4,793,808 | 12/1988 | Kirsch . | |
| 4,826,434 | 5/1989 | Krueger | 433/174 |
| 4,863,383 | 9/1989 | Grafelman . | |
| 5,073,111 | 12/1991 | Daftary | 433/173 |
| 5,102,414 | 4/1992 | Kirsch | 606/73 |
| 5,217,462 | 6/1993 | Asnis et al. | 606/105 X |

FOREIGN PATENT DOCUMENTS

| | | | |
|---|---|---|---|
| 0282789 | 9/1988 | European Pat. Off. . | |
| 2589350 | 5/1987 | France . | |
| 2634369 | 1/1990 | France | 433/174 |
| 0453048 | 11/1927 | Germany | 411/397 |
| 2540077 | 4/1976 | Germany | 433/174 |
| 4012731 | 10/1990 | Germany . | |
| 4107606 | 9/1992 | Germany | 433/173 |
| 0679117 | 12/1991 | Switzerland | 433/173 |
| 1514365 | 10/1989 | U.S.S.R. | 433/174 |
| 0464208 | 4/1937 | United Kingdom | 411/397 |
| 1291470 | 11/1972 | United Kingdom . | |
| 2184357 | 6/1987 | United Kingdom . | |

*Primary Examiner*—David H. Willse
*Attorney, Agent, or Firm*—Hill, Steadman & Simpson

[57] ABSTRACT

An implant has an implant member which is implantable in a bone material and has an axial threaded bore at one end which receives a threaded element which may be an implant post, an implant extension or a post for attachment by means of a screw connection. The threaded element has a head with a diameter greater than an outer diameter of the implant member adjacent the one end and the head has a pressing surface extending substantially at right angles to the axis of the implant member and beyond the outer diameter of the implant member. The head also has a circular recess between the pressing surface and the outer threads of the threaded element, which recess will receive an edge of the one end of the implant member when the threaded element is received in the threaded bore to prevent body tissue from growing into any slit or crevice between the implant member and the threaded element.

13 Claims, 2 Drawing Sheets

IMPLANT WITH PRESSING SURFACE

This is a continuation of application Ser. No. 07/969,857, filed as PCT/DE92/00291, Apr. 7, 1992, published as WO92/20298, Nov. 26, 1992, now abandoned.

BACKGROUND OF THE INVENTION

The invention relates to an implant with an implant member implantable in bone material and the implant member has an internal thread for receiving an implant post, an implant extension, a post for attachments, etc. by means of a screw connection.

For use in the jaw region such an implant is e.g. known from EP 0 216 031 A1 and has proved very satisfactory in practice.

However, in certain cases it is necessary, prior to the introduction of the member into the bone, to initially compensate for bone deficiencies in the region which deficiencies may be defects, cracks, etc. This compensation generally takes place in that correspondingly dimensioned bone portions are fixed to or on existing bone substance until they have firmly grown into the existing bone substance. A disadvantage is that a considerable time must elapse before new bone surgical manipulations can take place in this region, e.g. for introducing such an implant member, because in response to stresses the freshly grown in bone portions naturally have a tendency over a long period to become detached and to tear at their previous contact faces.

SUMMARY OF THE INVENTION

The problem of the invention is therefore to further develop the known implant in such a way that, in addition to its basic function, it can simultaneously be used for fixing to existing bone substance or structure any bone portions placed on or between the implant and the existing bone structure.

According to the invention this problem is solved in that a pressing surface which extends substantially at right angles to the axis of the implant member and over and beyond its cross-sectional or outer peripheral surface, is provided on the member or is connectable thereto. This pressing surface, which is provided on or connectable to the implant member makes it possible during the implanting thereof in existing, firm bone substance to simultaneously fix in a simple and effective manner bone portions for compensating any deficiencies that are present.

It is particularly preferable for the pressing surface to be formed by the projecting length of the screw head of a screw to be screwed into the internal thread of the implant member. This makes it possible to use a substantially conventional member for implants of the aforementioned type, in whose internal thread is screwed a corresponding screw and whose projecting screw head permits the corresponding fixing of the bone portions. After the latter have grown in the screw can be removed from the member and the implant member can be used for its basic function, i.e. for receiving an implant post or the like.

It is possible through a preferably provided thread at the distal end of the implant member to fix to existing bone substance a transplant, which is traversed by the implant member. The transplant and the bone to which the transplant is fixed will grow into the implant member, which is of a biocompatible material, to releasably anchor the implant member in the bore.

According to a preferred construction of the thread, the thread can be provided in the form of a wood screw thread with considerable depth and pitch and the shank terminates in a tip or point. Such a thread construction is always appropriate when it is not possible or useful to carry out special preparatory measures in the bone, e.g. by inserting a sleeve with a thread or cutting a thread directly into the jaw material.

In a further preferred construction, the thread is constructed as an acme or trapezoidal thread, particularly a symmetrical acme thread. This construction avoids the sharp edges occurring with a V-thread and makes it possible to screw in the member according to the tension flange principle so that the implant member is then securely held in place.

It is very advantageous if the thread has portions milled out as a pie-shaped notch which extend over all or part of the thread length. The portions act as a chip groove for the self-tapping thread. Advantageously the milled-out portions have a domed or curved edge and a straight edge in the substantially axial direction. The domed edge and the straight edge pass in such a way that the former is always trailing on screwing in, whereas the latter is the leading edge on screwing the member into the bone.

It is also preferred for the screw head to have a slot, which terminates inward of the screw head edge, so that the member together with the screw having the pressing surface can be turned into the bone without there being any risk of a screwdriver slipping or causing injury during this manipulation.

It is further proposed with regards to the screw that it has a circular recess for receiving the upper edge of the implant member. Such a circular recess ensures that the interior of the implant member is effectively sealed against the surrounding area, which is mainly necessary for hygienic reasons. However, it has the further advantage that part of the implant member is exposed on subsequently removing the screw. It is consequently unnecessary to free the member from any grown-on bone or tissue material.

It is also proposed that the member be made from titanium. The member is preferably provided with a plasma coating of hydroxyl apatite or the like or is mechanically and/or chemically roughened. Such a coating or roughening has the advantage that the bone tissue adheres very well thereto, which facilitates the growing of the bone into or onto the implant member. Since this is not necessarily desired in the area of the member where it is inserted in the circular recess of the screw and might even impede the sealing action, it is advantageous for there to be no coating or roughening in this area.

Further features and advantages of the invention can be gathered from the following description of a non-limitative embodiment, the claims and the attached drawings.

BRIEF DESCRIPTION OF THE DRAWINGS

FIG. 1 shows the implant member 10 with an internal threaded bore 11 which receives the screw 20 with its pressing surface 28 on the bottom of the screw head. As described hereinbefore, the pressing surface 28, which extends laterally beyond an outer surface 13 of the implant member 10, is used for pressing and fixing transplant material placed on the existing bone material or between the surface 28 and then existing bone material. The transplant material is preferably also provided with a hole, which is traversed by the member 10, so that in this way a fixing in the lateral direction is also achieved.

Figure 1:
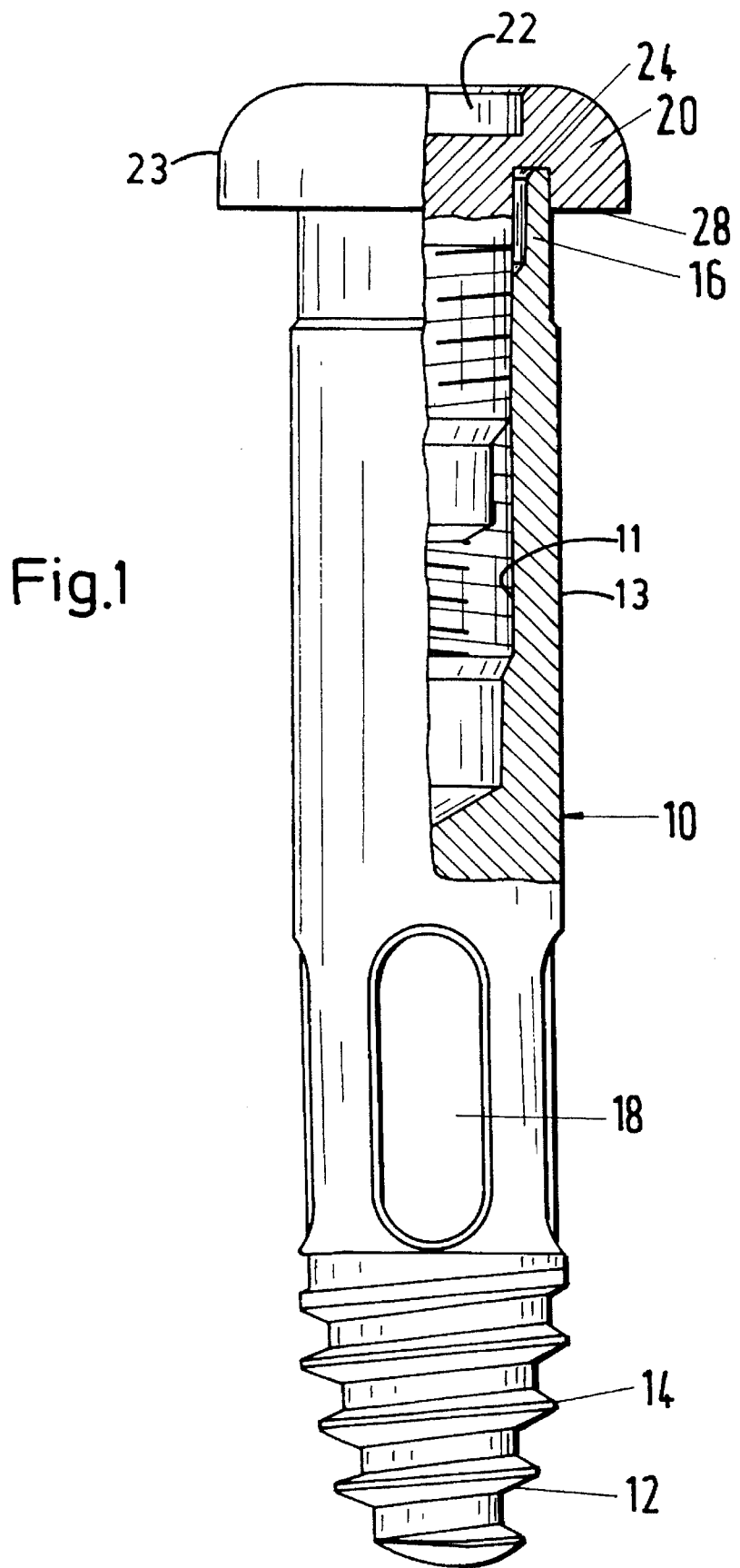
FIG. 1 is a side view with portions broken away of a complete implant member with a screw screwed into it.

It is clearly possible to see at the lower end of the implant member 10 the thread 14 with the flanks 12 which thread 14 extends towards the tip of the implant member. The inventive implant is designed in accordance with the tension flange principle, which is particularly suitable here, because the implant is consequently easy to screw in and ensures a firm seating. In addition, in the lower region of the implant member 10 it is possible to see the lacunas or depressions 18 positioned there and into which bone material can grow during healing for better anchoring.

The upper edge 16 of the implant member 10 fits or sinks into the circular recess 24 of the screw 20. The part 16 of the member which has been lowered into the screw head will always project out of the bone, because the bone surface is defined by the pressing surface 28, so that it is subsequently easy to fix an implant post or the like in the threaded bore 11 of the member 10.

Figure 2:
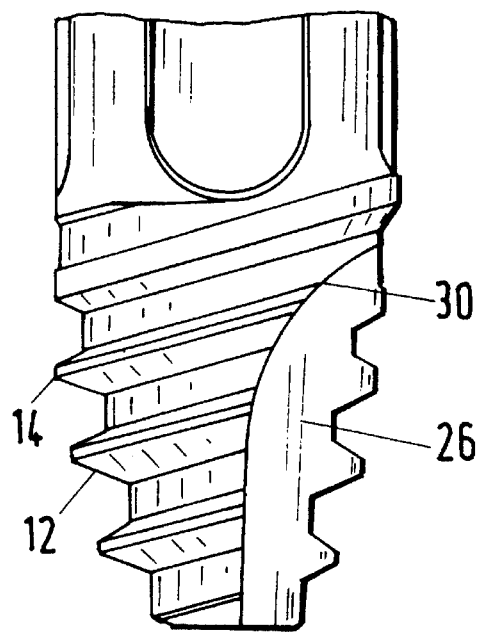
FIG. 2 is a side view of an end of the implant member with a thread having a milled-out portion with a curved surface to form a curved edge.
Figure 3:
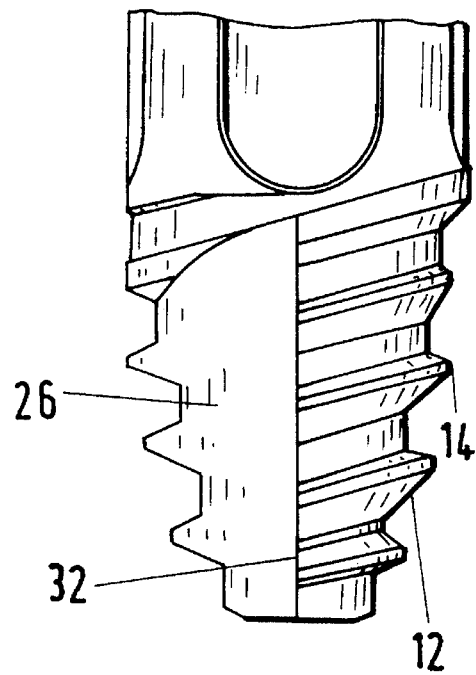
FIG. 3 is a side view rotated 90° of the end of FIG. 2 showing the planar surface forming the straight edge of the portion.

FIGS. 2 and 3 show in detail the thread 14. It is also possible to see the milled-out portion 26, which has a straight edge formed by a planar surface 32 and a domed edge or curved edge formed by a curved surface 20, which portion 26 serve as a chip groove for the self-tapping thread. On screwing in the thread the domed or curves edge is at the trailing side, whilst the milled-straight edge is on the leading side in the screwing in direction.

Figure 4:
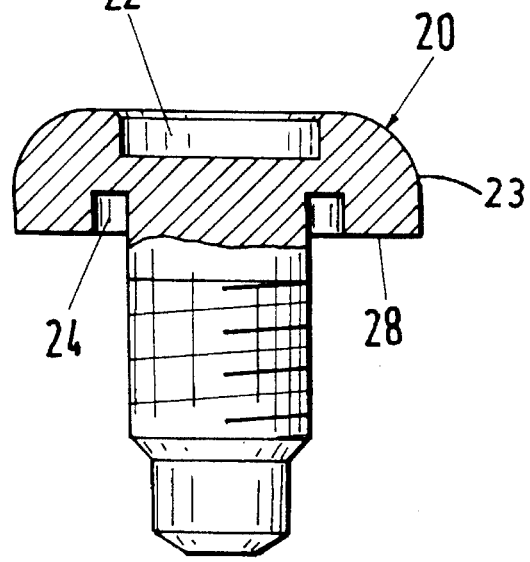
FIG. 4 is a side view with portions broken away of a screw for sealing the implant member on tis end that extends out of the jaw.
Figure 5:
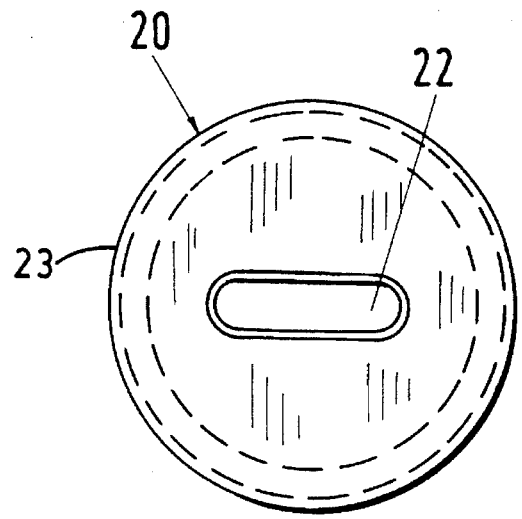
FIG. 5 is a plan view of the screw of FIG. 4.

The screw 20 for closing the internal thread running axially in the member 10 is shown in side view in FIG. 4 and partly in sectional view. However, for simplification reasons the thread is not shown. However, the circular recess 24 and the slot 22, which is used for screwing the member 10 into the bone and for unscrewing the screw 20 after the member 10 is anchored by the growing bone, are readily visible. FIG. 5, which is a plan view of the head of the screw 20 makes it clear that the slot 22 terminates inward of the periphery surface or edge 23 of said head.

The features of the invention disclosed in the description, drawings and claims can be essential to the realization of the different embodiments of the invention, either singly or in random combination.

We claim:

1. An implant member, which is implantable in a bone material, in combination with a removable screw, said implant member being of a biocompatible material having an outer surface and an internal threaded bore extending from one end of the implant member along an axis of the implant member toward another end of the member for receiving an outwardly threaded element including an implant post, an implant extension, or a post for attachment by means of a screw connection, said implant member having an external thread at the other end, said external thread having at least one pie-shaped notch which extends over at least a part of the length of the external thread and has a domed edge and a straight edge extending substantially in the axial direction, said removable screw having outer threads for provisional introduction into the internally threaded bore instead of the outwardly threaded element, said screw having a head with a diameter greater than the largest outer diameter of the implant member adjacent said one end, said head having means for fixing transplant bone material including a pressing surface extending substantially at a right angle to the axis of the implant member and beyond the largest outer diameter of said implant member, said head having a circular recess between the pressing surface and the outer thread of said screw for receiving an edge of the one end of the implant member when the screw is received in the threaded bore, whereby during the introduction of the screw, the internally threaded bore of the implant member is effectively sealed against the surrounding area and after removal of the screw, the edge of the one end is freely exposed.

2. An implant member and screw according to claim 1, wherein the external thread of said implant member is constructed in the manner of a wood screw thread with considerable depth and pitch and the other end of the implant member has a pointed tip.

3. An implant member and screw according to claim 2, wherein the external thread of the implant member is an acme thread.

4. An implant member and screw according to claim 1, wherein the head of the screw has a top surface with a slot terminating inward from an outer periphery of the head.

5. An implant member and screw according to claim 1, wherein the implant member is made from titanium and has a roughened outer surface except for the one end, which is received in the circular recess.

6. An implant member and screw according to claim 1, wherein the implant member is made of titanium and has a plasma coating of hydroxyl apatite on the outer surface except for the one end, which is received in the circular recess.

7. An implant member and screw according to claim 1, wherein the implant member is made of titanium.

8. An implant member and screw according to claim 7, wherein the outer surface of the implant member has a plasma coating of hydroxyl apatite.

9. An implant member and screw according to claim 7, wherein the outer surface of the implant member is a roughened-out surface.

10. A combination of an implant member and removable screw, said implant member being of a biocompatible material, being implantable in a bone material and having an outer surface for bone material to grow upon, said member having an internal threaded bore extending from one end of the member along an axis of the member for receiving an outwardly threaded element including an implant post, an implant extension, or a post for attachment by means of a screw connection, said implant member having an external thread at a second end, said external thread having a pie-shaded notch which extends over at least part of the length of the external thread and has a domed edge and a straight edge extending substantially in the axial direction, and said removable screw having an outer thread and being for provisional introduction into the internally threaded bore instead of the outwardly threaded element, said screw having a head with a diameter greater than the largest outer diameter of the implant member, said head having means for fixing transplant bone material including a pressing surface extending substantially at a right angle to the axis of the implant member and beyond the largest outer diameter of said implant member, said head having a circular recess between the pressing surface and the outer thread of said screw for receiving an edge of the one end of the implant member when the screw is received in the threaded bore, so that during the introduction of the screw, the internally threaded bore of the implant member is effectively sealed against the surrounding area and after, removal of the screw, the edge of the one end is freely exposed.

11. A combination according to claim 10, wherein the external thread is constructed in the manner of a wood screw thread with considerable depth and pitch and the second end of the implant member has a pointed tip.

12. A combination according to claim 10, wherein the head has a top surface with a slot terminating inward from an outer periphery of the head of the screw.

13. A combination according to claim 10, wherein the implant member is made from titanium and has a roughened outer surface except for the one end, which is received in the circular recess.

* * * * *